United States Patent
Winter et al.

[11] Patent Number: 5,990,331
[45] Date of Patent: Nov. 23, 1999

[54] METALLOCENES CONTAINING PARTIALLY HYDROGENATED P-LIGANDS

[75] Inventors: Andreas Winter, Glashütten; Roland Zenk, Bad Soden; Volker Fraaije, Frankfurt; Frank Küber, Oberursel, all of Germany

[73] Assignee: Targor GmbH, Ludwigshafen, Germany

[21] Appl. No.: 08/963,570

[22] Filed: Oct. 31, 1997

[30] Foreign Application Priority Data

Oct. 31, 1996 [DE] Germany .................. 196 44 041

[51] Int. Cl.$^6$ .................. C07F 17/00; C08F 4/643; B01J 31/00

[52] U.S. Cl. .................. 556/9; 556/12; 556/14; 556/19; 556/21; 556/22; 556/53; 556/58; 556/43; 502/103; 502/117; 502/152; 526/129; 526/160; 526/943

[58] Field of Search .................. 556/9, 12, 14, 556/19, 21, 22, 53, 58, 43; 502/103, 117, 152; 526/129, 160, 943

[56] References Cited

U.S. PATENT DOCUMENTS 5,510,502  4/1996  Sugano et al. .................. 556/11

FOREIGN PATENT DOCUMENTS 0 611 772 A2  8/1994  European Pat. Off. .

Primary Examiner—Porfirio Nazario-Gonzalez

[57] ABSTRACT

The present invention relates to a metallocene of the formula I,

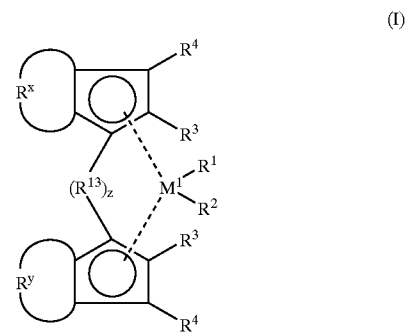

for preparing polyolefins, where $M^1$ is preferably Zr, Hf or Ti, $R^1$ and $R^2$ are each a hydrogen atom, a $C_1$–$C_3$-alkyl group, a $C_1$–$C_3$-alkoxy group, a $C_6$–$C_8$-aryl group, a $C_6$–$C_8$-aryloxy group, a $C_2$–$C_4$-alkenyl group, a $C_7$–$C_{10}$-arylalkyl group, a $C_7$–$C_{12}$-alkylaryl group, a $C_8$–$C_{12}$-arylalkenyl group or chlorine, $R^3$ is a chlorine atom, a $C_1$–$C_3$-alkyl group, a $C_2$–$C_4$-alkenyl group, a $C_6$–$C_8$-aryl group, an $NR^{16}_2$, $SR^{16}$, $OSiR^{16}_3$, $SiR^{16}_3$ or $PR^{16}_2$ radical where $R^{16}$ is chlorine, a $C_1$–$C_4$-alkyl group or a $C_6$–$C_8$-aryl group. $R^4$ is a hydrogen atom, $R^{13}$ is —$(R^{14}M^2R^{15})$—, —$(R^{14}CR^{15})$—$(R^{14}CR^{15})$—, —$(R^{14}CR^{15})$—$(R^{14}M^2R^{15})$— or —$(R^{14}CR^{15})$—, where $R^{14}$ and $R^{15}$ are each a hydrogen atom, chlorine, an Si(methyl)$_3$ group, an N(methyl)$_2$ group, an N(phenyl)$_2$ group, an Si(phenyl)$_3$ group, a B(methyl)$_2$ group, a B(phenyl)$_2$ group, a $C_1$–$C_4$-alkyl group, in particular a methyl group, a $CF_3$ group, a $C_6$–$C_{12}$-aryl group, a pentafluorophenyl group, a $C_1$–$C_4$-alkoxy group, in particular a methoxy group, a $C_2$–$C_4$-alkenyl group, a $C_7$–$C_{10}$-arylalkyl group, a $C_8$–$C_{12}$-arylalkenyl group or a $C_7$–$C_{12}$-alkylaryl group, or $R^{14}$ and $R^{15}$ together with the atoms connecting them form a ring, $M^2$ is silicon or germanium, z is 0 or 1, $R^x$ and $R^y$ are identical where $R^5$ to $R^9$ are as defined for $R^{14}$, and l+m+n+o+p≧2 and ≦5, and l+n+p is ≧1, where l, n, m, o or p can be 0, 1, 2 or 3 or $R^5$ to $R^9$ together with the atoms connecting them form one or more rings.

19 Claims, No Drawings

METALLOCENES CONTAINING PARTIALLY HYDROGENATED P-LIGANDS

The present invention relates to a metallocene containing a partially hydrogenated π ligand system and the use of at least one such metallocene for preparing polyolefins.

EP-A-576 970 discloses metallocenes which can convert olefins, in particular propylene, into isotactic polyolefins, in particular isotactic polypropylenes, with very high catalyst activity and very high stereospecificity.

It is an object of the present invention to provide a metallocene which, at very high polymerization activity, at the same time makes possible the preparation of polymers with reduced stereospecificity. A further object of the present invention is to provide an economical and environmentally friendly process for preparing polymers with reduced stereospecificity.

This object is achieved by a metallocene of the formula I whose π ligand system is partially hydrogenated

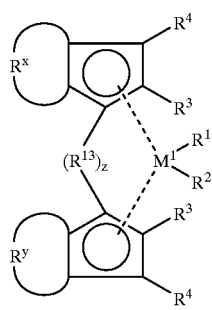

(I)

where $M^1$ is a metal of group IVb, Vb or VIb of the Periodic Table, $R^1$ and $R^2$ are identical or different and are each a hydrogen atom, a $C_1$–$C_{40}$-group such as a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, an OH group or a halogen atom, $R^3$ and $R^4$ are identical or different and are each a hydrogen atom, a halogen atom, a $C_1$–$C_{20}$-group, such as a $C_1$–$C_{10}$-alkyl group, a $C_2$–$C_{10}$-alkenyl group or a $C_6$–$C_{10}$-aryl group, an $NR^{16}{}_2$, $SR^{16}$, $OSiR^{16}{}_3$, $SiR^{16}{}_3$ or $PR^{16}{}_2$ radical, where $R^{16}$ is a halogen atom, a $C_1$–$C_{10}$-alkyl group or a $C_6$–$C_{10}$-aryl group, $R^{13}$ is a bridge such as

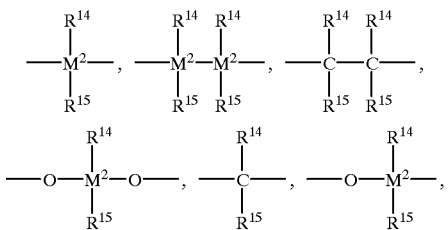

-continued

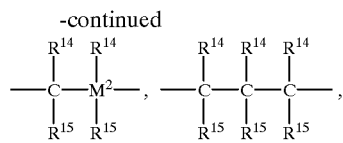

$=BR^4$, $=AlR^{14}$, —Ge—, —O—, —S—, =SO, $=SO_2$, $=NR^{14}$, =CO, $=PR^{14}$ or $=P(O)R^{14}$, where $R^{14}$ and $R^{15}$ are identical or different and are each a hydrogen atom, a halogen atom or a $C_1$–$C_{40}$-group such as an $Si(C_1$–$C_{10}$-alkyl$)_3$ group, an $Si(C_6$–$C_{20}$-aryl$)_3$ group, an $N(C_1$–$C_{10}$-alkyl$)_2$ group, an $N(C_6$–$C_{20}$-aryl$)_2$ group, a $B(C_1$–$C_{10}$-alkyl$)_2$ group, a $B(C_6$–$C_{20}$-aryl$)_2$ group, a $C_1$–$C_{10}$-alkyl group, a $C_1$–$C_{10}$-fluoroalkyl group, a $C_6$–$C_{20}$-aryl group, a $C_6$–$C_{20}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{14}$ and $R^{15}$ together with the atoms connecting them form a ring system, $M^2$ is silicon, germanium or tin and z is 0 or 1, $R^x$ and $R^y$ are identical or different and are a group

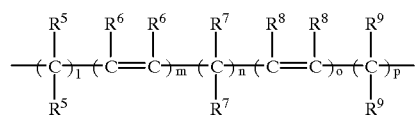

where $R^5, R^6, R^7, R^8$ and $R^9$ are identical or different and are each a hydrogen atom, a halogen atom or a $C_1$–$C_{40}$-group such as an $Si(C_1$–$C_{10}$-alkyl$)_3$ group, an $Si(C_6$–$C_{20}$-aryl$)_3$ group, an $N(C_1$–$C_{10}$-alkyl$)_2$ group, an $N(C_6$–$C_{20}$-aryl$)_2$ group, a $B(C_1$–$C_{10}$-alkyl$)_2$ group, a $B(C_6$–$C_{20}$-aryl$)_2$ group, a $C_1$–$C_{10}$-alkyl group, a $C_1$–$C_{10}$-fluoroalkyl group, a $C_6$–$C_{20}$-aryl group, a $C_6$–$C_{20}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or in each case two radicals $R^5, R^6, R^7, R^8$ and $R^9$ together with the atoms connecting them form a ring system, and $2 \leq l+m+n+o+p \leq 6$ and $l+n+p \geq 1$, where l, m, n, o and p can be 0, 1, 2, 3 or 4 and at least one of the indices m and o is not equal to 0, with the exception of the case where m=0, o=0, and l+n+p=4 and likewise with the exception of the case where l=0, n=0, p=0 and m+o=2.

Alkyl can be straight-chain or branched alkyl, halogen (halogenated) is, in particular, fluorine, chlorine, bromine or iodine, preferably fluorine or chlorine. The term ring system encompasses monocyclic and polycyclic ring systems which can be unsubstituted or substituted. Radicals having the same index can also be identical or different from one another.

For the metallocene of the formula I, it is preferred that $M^1$ is preferably Zr, Hf or Ti, particularly preferably Zr, $R^1$ and $R^2$ are identical or different, preferably identical, and are each a hydrogen atom, a $C_1$–$C_{10}$-, preferably $C_1$–$C_4$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{12}$-alkylaryl group, a $C_8$–$C_{40}$-, preferably $C_8$–$C_{12}$- arylalkenyl group or a halogen atom, preferably chlorine. In particular $R^1$ and $R^2$ are each a $C_1$–$C_{10}$-alkyl group or a halogen atom.

$R^3$ are preferably identical and are each a halogen atom, preferably chlorine, a $C_1$–$C_{10}$-, preferably $C_1$–$C_4$-alkyl group, a $C_2$–$C_{10}$-, preferably $C_2$–$C_4$-alkenyl group, a $C_6$–$C_{10}$-, preferably $C_6$–$C_8$-aryl group, an $NR^{16}_2$, $SR^{16}$, $OSiR^{16}_3$, $SiR^{16}_3$ or $PR^{16}_2$ radical, where $R^{16}$ is a halogen atom, preferably chlorine, a $C_1$–$C_{10}$-, preferably $C_1$–$C_4$-alkyl group or a $C_6$–$C_{10}$-, preferably $C_6$–$C_8$-aryl group. In particular, $R^3$ is a $C_1$–$C_{10}$-alkyl group.

$R^4$ are preferably identical and are each a hydrogen atom. $R^{13}$ is preferably

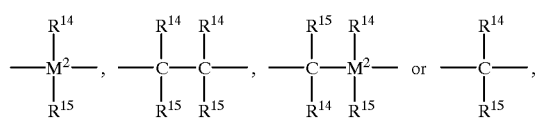

where
$R^{14}$ and $R^{15}$ are identical or different and are each a hydrogen atom, a halogen atom, preferably chlorine, an $Si(C_1$–$C_{10}$-alkyl$)_3$ group, preferably an Si(methyl)$_3$ group, an $N(C_1$–$C_{10}$-alkyl$)_2$, preferably an N(methyl)$_2$ group, an $N(C_6$–$C_{10}$-aryl$)_2$ group, preferably an N(phenyl)$_2$ group, an $Si(C_6$–$C_{10}$-aryl$)_3$ group, preferably an Si(phenyl)$_3$ group, a $B(C_6$–$C_{10}$-alkyl$)_2$ group, preferably a B(methyl)$_2$ group, a $B(C_6$–$C_{10}$-aryl$)_2$ group, preferably a B(phenyl)$_2$ group, a $C_1$–$C_{10}$-, preferably $C_1$–$C_4$-alkyl group, in particular a methyl group, a $C_1$–$C_{10}$-fluoroalkyl group, preferably a $CF_3$ group, a $C_6$–$C_{20}$-, preferably $C_6$–$C_{12}$-aryl group, a $C_6$–$C_{20}$-fluoroaryl group, preferably a pentafluorophenyl group, a $C_1$–$C_{10}$-, preferably $C_1$–$C_4$-alkoxy group, in particular a methoxy group, a $C_2$–$C_{10}$-, preferably $C_2$–$C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group or a $C_7$–$C_{40}$-, preferably $C_7$–$C_{12}$-alkylaryl group, or $R^{14}$ and $R^{15}$ together with the atoms connecting them form a ring system. In particular, $R^{14}$ and $R^{15}$ are each a $C_1$–$C_{10}$-alkyl group or a $C_8$–$C_{10}$-aryl group.

$M^2$ is silicon, germanium or tin, preferably silicon or germanium, and z is, in particular, equal to 1.

$R^x$ and $R^y$ are preferably identical and are each a group

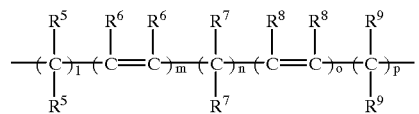

where
$R^5, R^6, R^7, R^8$ and $R^9$ are identical or different and are each preferably a hydrogen atom, a halogen atom, preferably chlorine, an $Si(C_1$–$C_{10}$-alkyl$)_3$ group, preferably an Si(methyl)$_3$ group, an $N(C_1$–$C_{10}$-alkyl$)_2$ group, preferably an N(methyl)$_2$ group, an $N(C_6$–$C_{10}$-aryl$)_2$ group, preferably an N(phenyl)$_2$ group, an $Si(C_6$–$C_{10}$-aryl$)_3$ group, preferably an Si(phenyl)$_3$ group, a $B(C_6$–$C_{10}$-alkyl$)_2$ group, preferably a B(methyl)$_2$ group, a $B(C_6$–$C_{10}$-aryl$)_2$ group, preferably a B(phenyl)$_2$ group, a $C_1$–$C_{10}$-, preferably $C_1$–$C_4$-alkyl group, in particular a methyl group, a $C_1$–$C_{10}$-fluoroalkyl group, preferably a $CF_3$ group, a $C_6$–$C_{20}$-, preferably $C_6$–$C_4$-aryl group, a $C_6$–$C_{20}$-fluoroaryl group, preferably a pentafluorophenyl group, a $C_1$–$C_{10}$-, preferably $C_1$–$C_4$-alkoxy group, in particular a methoxy group, a $C_2$–$C_{10}$-, preferably $C_2$–$C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group or a $C_7$–$C_{40}$-, preferably $C_7$–$C_{12}$-alkylaryl group, or in each case two radicals $R^5$, $R^6$, $R^7$, $R^8$ and $R^9$ together with the atoms connecting them form a ring system. In particular, $R^5, R^6, R^7, R^8$ and $R^9$ are each a hydrogen atom, a $C_1$–$C_{10}$-alkyl group, a $C_6$–$C_{20}$-aryl group or in each case two radicals $R^5$, $R^6$, $R^7$, $R^8$ and $R^9$ together with the atoms connecting them form a ring system.

It is preferred that $2 \leq l+m+n+o+p \leq 5$, and l, n, m, o and p are preferably 0, 1, 2 or 3.

Very particular preference is given to compounds of the formula I in which $M^1$ is zirconium or hafnium, $R^1$ and $R^2$ are identical and are each a halogen atom or a $C_1$–$C_4$-alkyl group, $R^3$ are identical and are each a $C_1$–$C_4$-alkyl group, $R^4$ are identical and are each a hydrogen atom, $R^{13}$ is

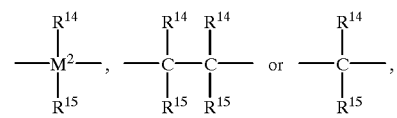

where $M^2$ is silicon or germanium, $R^{14}$ and $R^{15}$ are identical or different and are each a $C_1$–$C_{10}$-alkyl or $C_6$–$C_{10}$-aryl group, z is equal to 1 and $R^x$ and $R^y$ are identical and are four-membered groups, i.e. l+n+p=2 and m+o=1, for example
l=1, m=1, n=1, o and p=0 or
l=2, m=1, n, o and p=0 or
l=0, m=1, n=2, o and p=0.

The very particularly preferred metallocenes of the formula I are thus bisindenylzirconocenes which are partially hydrogenated in the six-membered ring:

(Ia)

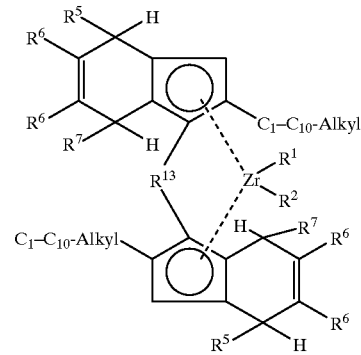

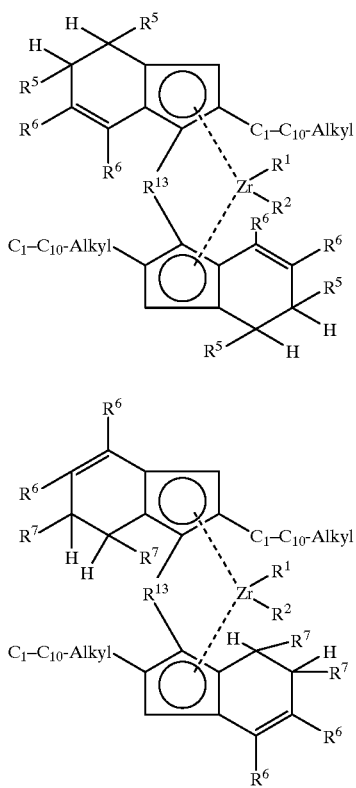

(Ib)

(Ic)

where

R$^1$, R$^2$, R$^5$, R$^6$, R$^7$ and R$^{13}$ are as defined in formula I and it is preferred that R$^5$, R$^6$ and R$^7$ are identical or different and are each a hydrogen atom or a C$_1$–C$_{40}$-group, in particular a C$_1$–C$_{20}$-hydrocarbon group such as C$_1$–C$_{10}$-alkyl or C$_6$–C$_{20}$-aryl, or in each case two radicals R$^5$, R$^6$ and/or R$^7$ can form a ring system.

Preferred metallocenes of the formula I are listed below by way of example but this listing does not imply a limitation. The ZrCl$_2$ derivatives are listed but the corresponding ZrMe$_2$ derivatives, HfCl$_2$ derivatives and HfMe$_2$ derivatives are likewise preferred.

The same applies to the replacement of the dimethylsilanediyl bridge by bridges such as (—CR$^{14}$R$^{15}$—)$_2$ (e.g. —CH$_2$—CH$_2$—), R$^{14}$R$^{15}$C, R$^{14}$R$^{15}$Ge or R$^{14}$R$^{15}$Si where R$^{14}$ and/or R$^{15}$ is/are not methyl.

Dimethylsilanediylbis(2-methyl-4,7-dihydro-1-indenyl)ZrCl$_2$
Dimethylsilanediylbis(2-methyl-4,5-dihydro-1-indenyl)ZrCl$_2$
Dimethylsilanediylbis(2-methyl-6,7-dihydro-1-indenyl)ZrCl$_2$
Dimethylsilanediylbis(2-methyl-4-phenyl-4,7-dihydro-1-indenyl)ZrCl$_2$
Dimethylsilanediylbis(2-methyl-4-phenyl-4,5-dihydro-1-indenyl)ZrCl$_2$
Dimethylsilanediylbis(2-methyl-4-phenyl-6,7-dihydro-1-indenyl)ZrCl$_2$
Dimethylsilanediylbis(2-methyl-4-(1-naphthyl)-4,7-dihydro-1-indenyl)ZrCl$_2$
Dimethylsilanediylbis(2-methyl-4-(1-naphthyl)-4,5-dihydro-1-indenyl)ZrCl$_2$
Dimethylsilanediylbis(2-methyl-4-(1-naphthyl)-6,7-dihydro-1-indenyl)ZrCl$_2$
Dimethylsilanediylbis(2-ethyl-4-phenyl-6,7-dihydro-1-indenyl)ZrCl$_2$
Dimethylsilanediylbis(2-isopropyl-4-phenyl-6,7-dihydro-1-indenyl)ZrCl$_2$
Dimethylsilanediylbis(2-isopropyl-4-(1-naphthyl)-6,7-dihydro-1-indenyl)ZrCl$_2$
Dimethylsilanediylbis(2-isopropyl-4-phenanthryl-6,7-dihydro-1-indenyl)ZrCl$_2$
Dimethylsilanediylbis(2-methyl-4,5-benzo-4,7-dihydro-1-indenyl)ZrCl$_2$
Dimethylsilanediylbis(2-methyl-4,5-benzo-4,5-dihydro-1-indenyl)ZrCl$_2$
Dimethylsilanediylbis(2-methyl-4,5-benzo-6,7-dihydro-1-indenyl)ZrCl$_2$
Dimethylsilanediylbis(2-ethyl-4,5-benzo-6,7-dihydro-1-indenyl)ZrCl$_2$
Dimethylsilanediylbis(2-isopropyl-4,5-benzo-6,7-dihydro-1-indenyl)ZrCl$_2$
Dimethylsilanediylbis(2-methyl-4,6-diisopropyl-4,7-dihydro-1-indenyl)ZrCl$_2$
Dimethylsilanediylbis(2-methyl-4,6-diisopropyl-6,7-dihydro-1-indenyl)ZrCl$_2$
Dimethylsilanediylbis(2-methyl-4,6-diisopropyl-4,5-dihydro-1-indenyl)ZrCl$_2$
Dimethylsilanediylbis(2,4,6-trimethyl-4,7-dihydro-1-indenyl)ZrCl$_2$
Dimethylsilanediylbis(2,4,6-trimethyl-4,5-dihydro-1-indenyl)ZrCl$_2$
Dimethylsilanediylbis(2,4,6-trimethyl-6,7-dihydro-1-indenyl)ZrCl$_2$
Dimethylsilanediylbis(2,4,6-triisopropyl-4,7-dihydro-1-indenyl)ZrCl$_2$
Dimethylsilanediylbis(2,4,6-triisopropyl-4,5-dihydro-1-indenyl)ZrCl$_2$
Dimethylsilanediylbis(2,4,6-triisopropyl-6,7-dihydro-1-indenyl)ZrCl$_2$
Dimethylsilanediylbis(2-ethyl-6,7-dihydro-1-indenyl)ZrCl$_2$
Dimethylsilanediylbis(2-ethyl-4,5-dihydro-1-indenyl)ZrCl$_2$
Dimethylsilanediylbis(2-ethyl-4,7-dihydro-1-indenyl)ZrCl$_2$
Dimethylsilanediylbis(2-isopropyl-6,7-dihydro-1-indenyl)ZrCl$_2$
Dimethylsilanediylbis(2-isopropyl-4,5-dihydro-1-indenyl)ZrCl$_2$
Dimethylsilanediylbis(2-isopropyl-4,7-dihydro-1-indenyl)ZrCl$_2$
Dimethylsilanediylbis(2,5,6-trimethyl-4,7-dihydro-1-indenyl)ZrCl$_2$
Dimethylsilanediylbis(2,5-dimethyl-4,7-dihydro-1-indenyl)ZrCl$_2$
Dimethylsilanediylbis(2,6-dimethyl-4,7-dihydro-1-indenyl)ZrCl$_2$
Dimethylsilanediylbis(2-methyl-α-acenaphth-6,7-dihydro-1-indenyl)ZrCl$_2$
Dimethylsilanediylbis(2-ethyl-α-acenaphth-6,7-dihydro-1-indenyl)ZrCl$_2$
Dimethylsilanediylbis(2-isopropyl-α-acenaphth-6,7-dihydro-1-indenyl)ZrCl$_2$
Dimethylsilanediylbis(2,4,7-trimethyl-4,7-dihydro-1-indenyl)ZrCl$_2$
Dimethylsilanediylbis(2,4,7-trimethyl-4,7-dihydro-1-indenyl)ZrCl$_2$
Dimethylsilanediylbis(2,4,7-trimethyl-4,5-dihydro-1-indenyl)ZrCl$_2$ The chiral metallocenes are used as a racemate for preparing highly isotactic polyolefins. However, it is also possible to use the pure R or S form. These pure stereoisomeric forms make it possible to prepare an optically active polymer. However, the meso form of the metallocenes should be separated off since the polymerization-active center (the metal atom) in these compounds is no longer chiral because of mirror symmetry at the central metal and therefore cannot produce an isotactic polymer. If the meso form is not separated off, atactic polymer is formed in addition to isotactic polymers. However, this can be thoroughly desirable for certain applications. It is thus also possible to use a rac/meso mixture of the metallocene of the formula I. Furthermore, mixtures of metallocenes of the formula I can also be used in the polymerization and may even be preferred. The separation of the stereoisomers is known in principle.

The metallocenes I can in principle be prepared according to the following reaction scheme:

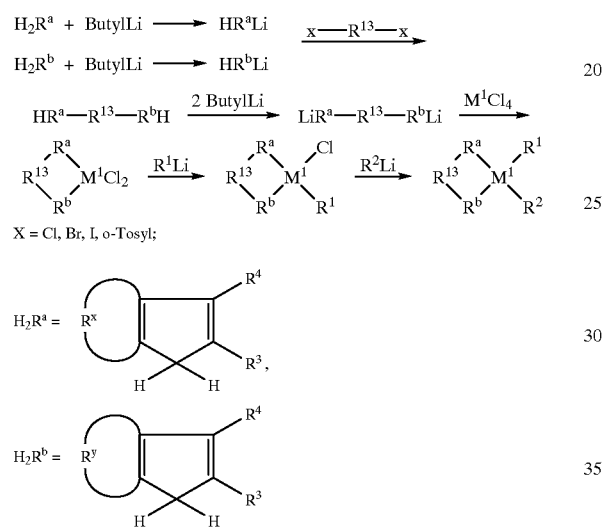

X = Cl, Br, I, o-Tosyl;

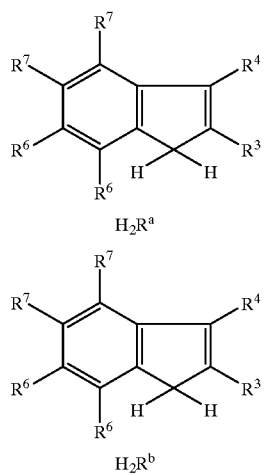

This preparation of the metallocene compounds is known in principle.

An alternative which is also preferred is first building up the metallocenes of the formula I using unsaturated radicals $R^x$ and $R^y$ and finally partially hydrogenating them in the presence of a catalyst. This is illustrated by an example in which the metallocene of the formula I is built up as outlined above. However, $H_2R^a$ and $H_2R^b$ are, for example,

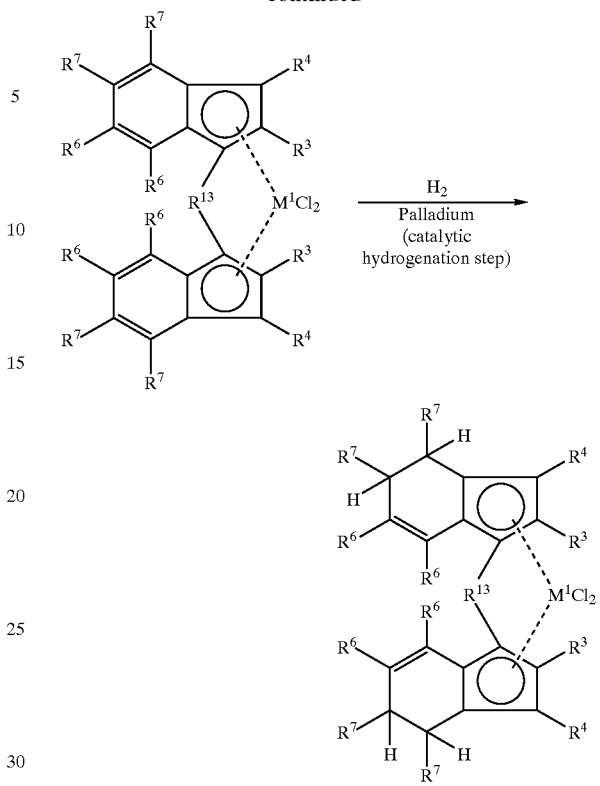

The hydrogenation step is carried out in anhydrous solvents such as toluene, xylene (as a mixture of isomers), o-xylene, m-xylene, p-xylene, mesitylene, tetralin, anisole, cumene, 1,2-diethylbenzene, 1,3-diethylbenzene, 1,4-diethylbenzene, 1-ethyl-2-methylbenzene, 1-ethyl-3-methylbenzene, 1-ethyl-4-methylbenzene; preference is given to anisole, toluene, benzene, xylenes (as a mixture or as pure substances) and tetralin.

Furthermore, oxygen-containing aprotic solvents such as aromatic or aliphatic ethers, for example anisole, ethyl phenyl ether, isopropyl phenyl ether, diethyl ether, di-n-butyl ether, tert-butyl methyl ether, tetrahydrofuran or dioxane, can also be used. In addition, esters of aliphatic or aromatic carboxylic acids can also be used as solvent, for example ethyl acetate and propyl butyrate.

It is also possible to use chlorinated hydrocarbons as solvent, for example dichloromethane. However, such solvents are less suitable for technical and ecological reasons and are thus less preferred.

The hydrogenation step is carried out at from 0 to 150° C., preferably from 15 to 100° C.

The hydrogen pressure is from 5 to 200 bar, preferably from 10 to 100 bar, in particular from 10 to 70 bar. The reaction time is from 10 minutes to 24 hours, preferably from 0.5 to 15 hours, in particular from 1 to 12 hours. The vessel used for the hydrogenation can be, for example, a steel autoclave. Hydrogenation catalysts used are the compounds described in the literature for such reactions, for example platinum, platinum oxide, palladium or other customary transition metal catalysts. Particularly useful hydrogenation catalysts are compounds or elements which do not hydrogenate or only partially hydrogenate the solvent under the hydrogenation conditions employed. Examples of such hydrogenation catalysts are palladium on activated carbon, palladium on barium sulfate, palladium on aluminum oxide, palladium black, palladium sponge, platinum oxide, platinum black, platinum sponge. Preference is given to using palladium catalysts, in particular palladium on activated carbon. The halogen derivatives ($R^1=R^2$=halogen, for example Cl) thus obtained can be reacted with $R^1$Li and/or $R^2$Li where $R^1,R^2$=alkyl, aryl or, for example, alkenyl, according to the method outlined above to convert them into the corresponding alkyl, aryl or, for example, alkenyl derivatives of the formula I.

The metallocenes of the formula I can be used as catalyst components in olefin polymerization. Here, use is made of at least one metallocene of the formula I and also a cocatalyst which is preferably an aluminum or boron compound. In particular, the cocatalyst used is an aluminoxane, e.g. of the formula II and/or III, where n is an integer from 0 to 50, preferably from 10 to 35.

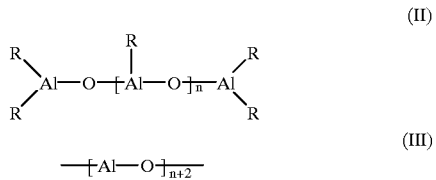

In general, the radicals R are identical or different and are each a $C_1$–$C_6$-alkyl group, a $C_1$–$C_6$-fluoroalkyl group, a $C_8$–$C_{18}$-alkyl group, a $C_6$–$C_{18}$-fluoroalkyl group, hydrogen or halogen.

The radicals R are preferably identical and are methyl, isobutyl, phenyl or benzyl, particularly preferably methyl.

If the radicals R are different, they are preferably methyl and hydrogen or alternatively methyl and isobutyl, where hydrogen or isobutyl is preferably present in a proportion of 0.01–40% (number of the radicals R). Instead of the aluminoxane, the cocatalyst used in the polymerization can be a mixture comprising aluminoxane and $AlR_3$, where R is as defined above.

The aluminoxane can be prepared in various ways by known methods. One of the methods is, for example, reacting an aluminum hydrocarbon compound and/or a hydridoaluminum hydrocarbon compound with water (gaseous, solid, liquid or bound—for example as water of crystallization) in an inert solvent (such as toluene). To prepare an aluminoxane having different alkyl groups R, two different trialkylaluminums ($AlR_3$+$AlR'_3$) corresponding to the desired composition are reacted with water (cf. S. Pasynkiewicz, Polyhedron 9 (1990) 429 and EP-A-302 424).

The exact three-dimensional structure of the aluminoxanes II and III is not known.

Regardless of the method of preparation, all aluminoxane solutions have in common a varying content of unreacted aluminum starting compound which is present in free form or as adduct.

It is possible to preactivate the metallocenes, in each case separately or together as a mixture, with an aluminoxane of the formula (II) and/or (III) before use in the polymerization reaction. This significantly increases the polymerization activity and improves the particle morphology of the polymer.

The preactivation of the metallocenes is carried out in solution. Preferably, the solid metallocenes are dissolved in a solution of the aluminoxane in an inert hydrocarbon. Suitable inert hydrocarbons are aliphatic or aromatic hydrocarbons. Preference is given to using toluene or a $C_6$–$C_{10}$-hydrocarbon.

The concentration of the aluminoxane in the solution is in the range from about 1% by weight to the saturation limit, preferably from 5 to 30% by weight, in each case based on the total solution. The metallocenes can be used in the same concentration, but they are preferably used in an amount of $10^{-4}$–1 mol per mol of aluminoxane. The preactivation time is from 1 minute to 60 hours, preferably from 5 to 60 minutes. The preactivation is carried out at a temperature of from $-78°$ C. to $100°$ C., preferably from $0°$ C. to $70°$ C.

The metallocenes can also be prepolymerized or applied to a support. The prepolymerization is preferably carried out using the (or one of the) olefin(s) used in the polymerization, but a different olefin can also be used.

Suitable supports are, for example, silica gels, aluminum oxides, solid aluminoxane, combinations of aluminoxane on a support such as silica gel or other inorganic support materials. Another suitable support material is a polymer powder, preferably polyolefin powder in finely divided form.

The novel metallocenes of the formula (I) can also be used in admixture with known metallocenes. Such mixtures preferably comprise the novel metallocenes of the formula (I) together with bisindenylzirconocenes in which the indenyl ligand is substituted by or fused to an alkyl or aryl radical in the 2; 2,4; 2,4,5; 2,4,5,6; 2,5; 2,6; 2,5,6 or 2,4,7 positions.

A further possible embodiment of the process of the invention comprises using a boron-containing salt-like compound of the formula $R_xNH_{4-x}BR'_4$ or the formula $R_3PHBR'_4$ as cocatalyst in place of or together with an aluminoxane. In these formulae, x=1, 2 or 3, R=alkyl or aryl, identical or different, and R'=aryl which may also be fluorinated or partially fluorinated. In this case, the catalyst comprises the reaction product of the metallocenes with one of the compounds mentioned (cf. EP-A-277 004).

To remove catalyst poisons present in the olefin, purification using an aluminum alkyl, for example $Al(i$-butyl$)_3$, $AlMe_3$ or $AlEt_3$, is advantageous. This purification can either be carried out in the polymerization system itself or the olefin is brought into contact with the Al compound and subsequently separated off again before addition to the polymerization system.

The polymerization can be a homopolymerization or copolymerization and can be carried out in a known manner in solution, in suspension or in the gas phase, continuously or batchwise, in one or more stages at a temperature of preferably from 0 to $200°$ C., in particular from 20 to $100°$ C. The compounds polymerized are olefins, preferably those of the formula $R^c$—CH=CH—$R^d$. In this formula, $R^c$ and $R^d$ are identical or different and are each a hydrogen atom or a $C_1$–$C_{20}$-hydrocarbon radical, e.g. an alkyl radical having from 1 to 14 carbon atoms. $R^c$ and $R^d$ together with the carbon atoms connecting them can also form a ring. Examples of olefins corresponding to the formula $R^c$—CH=CH—$R^d$ are ethylene, propylene, 1-butene, 1-hexene, 4-methyl-1-pentene, 1-octene, norbornene, ethylidenenorbornene or norbornadiene. In particular, propylene and ethylene or hexene are polymerized. In the polymerization of ethylene or the copolymerization of ethylene with one or more comonomers as defined above, preference is given to a metallocene of the formula (I) in which z=0. In the polymerization of higher olefins such as propylene with subordinate amounts of ethylene, preference is given to a metallocene of the formula (I) in which z=1. If necessary, hydrogen is added as molecular weight regulator.

The total pressure in the polymerization system is from 1 to 1000 bar. The polymerization is preferably carried out in the industrially particularly important pressure range from 5 to 64 bar.

In the polymerization, the metallocenes are employed in a concentration, based on the transition metal, of from $10^{-3}$ to $10^{-8}$ mol, preferably from $10^{-4}$ to $10^{-7}$ mol, of transition metal per dm$^3$ of solvent or per dm$^3$ of reactor volume. The aluminoxane or the aluminoxane/AlR$_3$ mixture is used in a concentration of from $10^{-5}$ to $10^{-1}$ mol, preferably from $10^{-4}$ to $10^{-2}$ mol, per dm$^3$ of solvent or per dm$^3$ of reactor volume. However, other concentrations are also possible in principle.

If the polymerization is carried out as a suspension or solution polymerization, an inert solvent customary for the Ziegler low-pressure process is used. For example, the polymerization is carried out in an aliphatic or cycloaliphatic hydrocarbon, for example butane, pentane, hexane, heptane, decane, isooctane, cyclohexane or methylcyclohexane.

It is also possible to use a petroleum or hydrogenated diesel oil fraction. Toluene can also be used. Preference is given to carrying out the polymerization in the liquid monomer.

If inert solvents are used, the monomers are metered in in gaseous or liquid form.

The polymerization time can be any desired, since the catalyst system to be used according to the invention displays only a slight time-dependent drop in the polymerization activity.

The process is notable for the fact that use of the metallocenes described in the industrially particularly important temperature range from 40 to 80° C. makes it possible to prepare, with a very high polymerization activity, polymers having a high molar mass of $M_w$>100 000 g/mol and a reduced polymer melting point. Regulation using relatively large amounts of hydrogen during the polymerization also enables the preparation of polymer waxes with very high catalyst activity.

The present invention is illustrated by the following examples.

EXAMPLES

Definitions:

VN=Viscosity number in cm$^3$/g $M_w$=Weight average molar mass in g/mol (determined by gel permeation chromatography)

$M_w/M_n$=Polydispersity (determined by gel permeation chromatography)

Melting point determination by means of DSC (20° C./min)

$n_{PE}$=mean "polyethylene" block length in the polymer chain (determined by $^{13}$C-NMR)

Metallocene syntheses

Example 1

4.0 g (9.0 mmol) of rac-dimethylsilanediylbis(2-methyl-4,5-benzindenyl)zirconium dichloride and 0.3 g (0.28 mmol) of palladium (10% on activated carbon) were suspended in 100 ml of toluene and hydrogenation was carried out at 70° C. and a hydrogen pressure of 30 bar. After 6 hours, the reaction mixture was filtered hot, extracted with 2000 ml of hot toluene and the extract was evaporated to 300 ml. The partially hydrogenated product rac-dimethylsilanediylbis(2-methyl-6,7-dihydro-4,5-benzindenyl)zirconium dichloride crystallized out at 0–5° C.

Yield: 2.6 g (4.5 mmol; 50%).

$^1$H-NMR (300 MHz, CDCl$_3$): d=7.42 (m, 2H); 7.3–7.14 (m, 4H); 7.2 (m, 2H); 6.96 (s, 2H); 2.82 (m, 2H); 2.25 (s, 6H); 1.02 (s, 6H).

Example 2

4.0 g (6.4 mmol) of rac-dimethylsilanediylbis(2-methyl-4-phenylindenyl)zirconium dichloride and 0.3 g (0.28 mmol) of palladium (10% on activated carbon) were suspended in 100 ml of toluene and hydrogenation was carried out at 70° C. and a hydrogen pressure of 50 bar. After 6 hours, the reaction mixture was filtered hot, extracted with 1600 ml of hot toluene and the extract was evaporated to 180 ml. The partially hydrogenated product rac-dimethylsilanediylbis(2-phenyl-6,7-dihydroindenyl)zirconium dichloride crystallized out at 0–5° C.

Yield: 1.9 g (3.0 mmol; 47%).

Example 3

4.0 g (7.3 mmol) of rac-1,2-ethanediylbis(2-methyl-4,5-benzindenyl)zirconium dichloride and 0.3 g (0.28 mmol) of palladium (10% on activated carbon) were suspended in 100 ml of toluene and hydrogenation was carried out at 70° C. and a hydrogen pressure of 30 bar. After 6 hours, the reaction mixture was filtered hot, extracted with 1800 ml of hot toluene and the extract was evaporated to 220 ml. The partially hydrogenated product rac-1,2-ethanediylbis(2-methyl-6,7-dihydro-4,5-benzindenyl)zirconium dichloride crystallized out at 0–5° C.

Yield: 2.9 g (5.3 mmol; 72%).

Polymerization Examples

Example 4

A dry 24 dm$^3$ reactor which had been flushed first with nitrogen and subsequently with propene was charged with 12 dm$^3$ of liquid propene. 35 cm$^3$ of methylaluminoxane solution in toluene (corresponding to 52 mmol of Al, mean degree of oligomerization n=20) were added and the mixture was stirred at 30° C. for 5 minutes. In parallel thereto, 1 mg of dimethylsilanediylbis(2-methyl-4,5-benzo-6,7-dihydro-1-indenyl)zirconium dichloride (rac:meso ratio >20) was dissolved in 13.5 cm$^3$ of methylaluminoxane solution in toluene (corresponding to 20 mmol of Al) and preactivated for 5 minutes at 40° C. The solution was then injected into the reactor and the polymerization system was heated (over a period of 5 minutes) to 70° C. and held at this temperature for one hour by means of cooling. The polymerization was then stopped by addition of CO$_2$ gas, excess propene was vented and the polymer was dried in a high vacuum at 80° C. for 12 hours. This gave 1.84 kg of polymer, corresponding to a metallocene activity of 1840 kg of polypropylene/g of metallocene×h of polymerization time. The polymer had the following properties:

VN=127 cm$^3$/g; $M_w$=140,000 g/mol, $M_w/M_n$=2.1; melting point: 142° C.

Example 5

Example 4 was repeated at a polymerization temperature of 50° C. This gave 0.75 kg of polymer and the metallocene activity was thus 750 kg of PP/g of metallocene×h. VN=189 cm$^3$/g; $M_w$=232,000 g/mol, $M_w/M_n$=2.3; melting point: 141° C.

Comparative Examples 1 and 2

Examples 4 and 5 were repeated using the metallocene dimethylsilanediylbis(2-methyl-4,5-benzo-1-indenyl)

zirconium dichloride (rac:meso ratio >20). Comparative Example 1 corresponds to the polymerization temperature of 70° C. and Comparative Example 2 corresponds to the polymerization temperature of 50° C.

Results of Comparative Example 1

0.61 kg of polymer were obtained, corresponding to a metallocene activity of 610 kg of PP/g of metallocene×h.

VN=296 cm$^3$/g; M$_w$=358,500 g/mol, M$_w$/M$_n$=2.0;
melting point: 151° C.

Results of Comparative Example 2

0.27 kg of polymer were obtained, corresponding to a metallocene activity of 270 kg of PP/g of metallocene×h.

VN=504 cm$^3$/g; M$_w$=699,500 g/mol, M$_w$/M$_n$=2.1;
melting point: 153° C.

Example 6

A dry 24 dm$^3$ reactor which had been flushed first with nitrogen and subsequently with propene was charged with 60 standard dm$^3$ of hydrogen and 12 dm$^3$ of liquid propene. 35 cm$^3$ of methylaluminoxane solution in toluene (corresponding to 52 mmol of Al, mean degree of oligomerization n=20) were then added and the mixture was stirred at 30° C. for 5 minutes. In parallel thereto, 0.5 mg of dimethylsilanediylbis(2-methyl-4,5-benzo-6,7-dihydro-1-indenyl)zirconium dichloride (rac:meso ratio >20) was dissolved in 13.5 cm$^3$ of methylaluminoxane solution in toluene (corresponding to 20 mmol of Al) and preactivated for 5 minutes at 40° C. The solution was then injected into the reactor and the polymerization system was heated (over a period of 5 minutes) to 70° C. and held at this temperature for one hour by means of cooling. The polymerization was then stopped by addition of CO$_2$ gas, excess propene was vented and the polymer was dried in a high vacuum at 80° C. for 12 hours. This gave 2.13 kg of polymer, corresponding to a metallocene activity of 4260 kg of polypropylene/g of metallocene×h of polymerization time. The polymer wax had the following properties:

VN=30 cm$^3$/g; M$_w$=187,000 g/mol, M$_w$/M$_n$=2.0;
melting point: 142° C.

Example 7

Example 6 was repeated at a polymerization temperature of 50° C. This gave 0.88 kg of polymer and the metallocene activity was thus 1760 kg of PP/g of metallocene×h.

VN=41 cm$^3$/g; M$_w$=346,000 g/mol, M$_w$/M$_n$=2.4;
melting point: 139° C.

Comparative Example 3

Example 7 was repeated using the metallocene dimethylsilanediylbis(2-methyl-4,5-benzo-1-indenyl) zirconium dichloride (rac:meso ratio >20). This gave 0.38 kg of polymer and the metallocene activity was thus 760 kg of PP/g of metallocene×h.

VN=31 cm$^3$/g; M$_w$=285,000 g/mol, M$_w$/M$_n$=2.7;
melting point: 150° C.

Example 8

Example 4 was repeated using the metallocene 1,2-ethanediylbis(2-methyl-4,5-benzo-6,7-dihydro-1-indenyl)zirconium dichloride (rac:meso ratio >20). This gave 2.24 kg of polymer, corresponding to a metallocene activity of 2240 kg of polypropylene/g of metallocene×h of polymerization time. The polymer had the following properties:

VN=117 cm$^3$/g; M$_w$=142,500 g/mol, M$_w$/M$_n$=2.4;
melting point: 143° C.

Example 9

Example 4 was repeated using the metallocene dimethylsilanediylbis(2-methyl-4-phenyl-6,7-dihydro-1-indenyl)zirconium dichloride (rac:meso ratio >20). This gave 1.64 kg of polymer, corresponding to a metallocene activity of 1640 kg of polypropylene/g of metallocene×h of polymerization time.

Comparative Example 4

Example 9 was repeated using the metallocene dimethylsilanediylbis(2-methyl-4-phenyl-1-indenyl) zirconium dichloride (rac:meso ratio >20). This gave 1.05 kg of polymer, corresponding to a metallocene activity of 1050 kg of polypropylene/g of metallocene×h of polymerization time.

Example 10

Example 4 was repeated using the metallocene dimethylsilanediylbis(2,5,6-trimethyl-4,7-dihydro-1-indenyl)zirconium dichloride (rac:meso ratio >20). This gave 0.18 kg of polymer, corresponding to a metallocene activity of 180 kg of polypropylene/g of metallocene×h of polymerization time.

Comparative Example 5

Example 10 was repeated using the metallocene dimethylsilanediylbis(2,5,6-trimethyl-1-indenyl)zirconium dichloride (rac:meso ratio >20). This gave 0.045 kg of polymer, corresponding to a metallocene activity of 45 kg of polypropylene/g of metallocene×h of polymerization time.

Comparative Example 6

Example 10 was repeated using the metallocene dimethylsilanediylbis(4,7-dimethyl-1-indenyl)zirconium dichloride (rac:meso ratio >20). This gave 0.27 kg of polymer, corresponding to a metallocene activity of 270 kg of polypropylene/g of metallocene×h of polymerization time.

Comparative Example 7

Example 10 was repeated using the metallocene dimethylsilanediylbis(4,7-dimethyl-4,5,6,7-tetrahydro-1-indenyl)zirconium dichloride (rac:meso ratio >20). This gave 0.16 kg of polymer, corresponding to a metallocene activity of 160 kg of polypropylene/g of metallocene×h of polymerization time.

Example 11

A dry 24 dm$^3$ reactor which had been flushed first with nitrogen and subsequently with propene was charged with 12 dm$^3$ of liquid propene. 35 cm$^3$ of methylaluminoxane solution in toluene (corresponding to 52 mmol of Al, mean degree of oligomerization n=20) were then added and the mixture was stirred at 30° C. for 5 minutes. In parallel thereto, 1 mg of dimethylsilanediylbis(2-methyl-4,5-benzo-6,7-dihydro-1-indenyl)zirconium dichloride (rac:meso ratio >20) was dissolved in 13.5 cm³ of methylaluminoxane solution in toluene (corresponding to 20 mmol of Al) and preactivated for 5 minutes at 40° C. The solution was then injected into the reactor and the polymerization system was heated (over a period of 3 minutes) to 50° C. and held at this temperature for one hour by means of cooling. During the polymerization, 50 g of ethylene were uniformly metered into the reactor. The polymerization was then stopped by addition of $CO_2$ gas, excess monomer was vented and the polymer was dried in a high vacuum at 80° C. for 12 hours. This gave 0.97 kg of polymer, corresponding to a metallocene activity of 970 kg of copolymer/g of metallocene x h of polymerization time. The copolymer contained 3.1% by weight of ethylene, the ethylene was incorporated randomly (NMR spectroscopy, $n_{PE}$=about 1.1) and the melting point was 129° C.

Example 12

A dry 150 dm³ reactor was flushed with nitrogen and charged at 20° C. with 80 dm³ of a petroleum fraction having a boiling range of 100–200° C. The gas space was then flushed free of nitrogen by pressurizing with 2 bar of propene and venting a total of 5 times. After 50 dm³ of liquid propene had been added, 20 cm³ of methylaluminoxane solution in toluene (corresponding to 100 mmol of Al, molar mass by cryoscopic determination=970 g/mol) were added and the contents of the reactor were heated to 50° C. A hydrogen content in the gas space of the reactor of 0.1% was set by metered addition of hydrogen and was later kept constant during the first polymerization stage by further metered addition. 8 mg of dimethylsilanediylbis(2-methyl-4,5-benzo-6,7-dihydro-1-indenyl)zirconium dichloride (rac:meso ratio >20) were dissolved in 32 cm³ of methylaluminoxane solution in toluene (corresponding to 50 mmol of Al) and after 10 minutes introduced into the reactor. In a first polymerization stage, polymerization was carried out at 55° C. for 4 hours. The reactor was then vented to a pressure of 2 bar and 2 kg of ethylene gas were fed in. This increased the reactor pressure to 7.3 bar and polymerization was continued at 45° C. for 8 hours, after which the reaction was stopped using $CO_2$ gas. This gave 17.8 kg of block copolymer, corresponding to a metallocene activity of 185.4 kg of polymer/g of metallocene×h. The polymer was fractionated. The homopolymer of the first polymerization stage had a melting point of 142° C.; the EPM rubber produced in the second polymerization stage had a glass transition temperature of −52° C., an ethylene content of 46% by weight and made up 22% of the total block copolymer.

Example 13
Preparation of the Supported Metallocene Catalyst 142 mg (0.24 mmol) of rac-dimethylsilanediylbis(2-methyl-4,5-benzo-6,7-dihydro-1-indenyl)zirconium dichloride were dissolved in 8.9 ml (41 mmol) of 30% strength MAO solution in toluene (Albemarle). The mixture was allowed to stand overnight at room temperature while being protected from light. The metallocene/MAO solution was subsequently diluted with 7.1 ml of toluene. 8 g of silica gel MS 948 from Grace Davison (calcined at 600° C.) were placed in a wide-mouthed vessel (glass beaker, stirred dish) and the diluted metallocene/MAO solution was added a little at a time while stirring (125% filling of the pore volume). After addition was complete, the mixture was stirred further for about 10 minutes. The solvent was removed under reduced pressure and the catalyst was dried to a residual solvent content of at most 5% by weight. This gave 11.65 g of an orange, free-flowing powder which, according to elemental analysis, contained 0.19% of Zr and 9.5% of Al.
Polymerization A dry 16 dm³ reactor which had been flushed first with nitrogen and subsequently with propene was charged with 10 dm³ of liquid propene and 2 standard dm³ of hydrogen. 8 ml of 20% strength triethylaluminum solution in Varsol (Witco) were added as scavenger and the mixture was stirred at 30° C. for 15 minutes. A suspension of 0.5 g of the supported metallocene catalyst in 20 ml of Exxsol was then introduced into the reactor, the polymerization system was heated to the polymerization temperature of 65° C. and held at 65° C. for 1 hour. The polymerization was stopped by venting the excess monomer and the polymer obtained was dried under reduced pressure. This gave 2.3 kg of polypropylene powder. The catalyst activity was 220 kg of PP/(mmol of Zr×h) or 4.6 kg of PP/(g of catalyst×h). The isotactic polypropylene prepared had the following properties:

m.p.=138° C.; $M_w$=138,000; $M_w/M_n$=2.6; VN=163 cm³/g;

bulk density=470 g/dm³; $d_{50}$=950 μm.

Example 14

Example 4 was repeated using the metallocene dimethylsilanediylbis(2-methyl-α-acenaphth-6,7-dihydro-1-indenyl)ZrCl₂ (see figure) (rac:meso ratio >17). The metallocene activity was 1930 kg of polypropylene/g of metallocene×h of polymerization time. The polymer had the following properties:

VN=157 cm³/g; $M_w$=172,500 g/mol, $M_w/M_n$=2.2;

melting point: 143° C.

Structural formula of the metallocene of Example 14

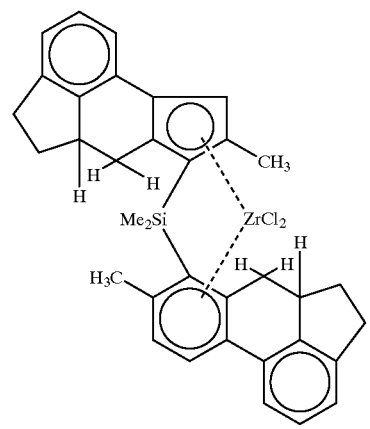

Example 15

Example 13 was repeated using a metallocene mixture consisting of 71 mg of the novel metallocene rac-dimethylsilanediylbis(2-methyl-4,5-benzo-6,7-dihydro-1-indenyl)zirconium dichloride and 75 mg of the known metallocene rac-dimethylsilanediylbis(2-methyl-4-phenyl-1-indenyl)zirconium dichloride. The catalyst activity was 198 kg of PP/(mmol of zirconium×h) or 4 kg of PP/(g of catalyst×h).

We claim:

1. A metallocene of the formula I

[Structure I]

where $M^1$ is a metal of group IVb, Vb or VIb of the Periodic Table, $R^1$ and $R^2$ are identical or different and are each a hydrogen atom, a $C_1$–$C_{40}$-group such as a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, an OH group or a halogen atom, $R^3$ and $R^4$ are identical or different and are each a hydrogen atom, a halogen atom, a $C_1$–$C_{20}$-group, such as a $C_1$–$C_{10}$-alkyl group, a $C_2$–$C_{10}$-alkenyl group or a $C_6$–$C_{10}$-aryl group, an $NR^{16}{}_2$, $SR^{16}$, $OSiR^{16}{}_3$, $SiR^{16}{}_3$ or $PR^{16}{}_2$ radical, where $R^{16}$ is a halogen atom, a $C_1$–$C_{10}$-alkyl group or a $C_6$–$C_{10}$-aryl group, $R^{13}$ is a bridge having the formula

[Bridge formulas]

$=BR^{14}$, $=AlR^{14}$, —Ge—, —O—, —S—, $=SO$, $=SO_2$, $=NR^{14}$, $=CO$, $=PR^{14}$ or $=P(O)R^{14}$, where $R^{14}$ and $R^{15}$ are identical or different and are each a hydrogen atom, a halogen atom or a $C_1$–$C_{40}$-group such as an Si($C_1$–$C_{10}$-alkyl)$_3$ group, an Si($C_6$–$C_{20}$-aryl)$_3$ group, an N($C_1$–$C_{10}$-alkyl)$_2$ group, an N($C_6$–$C_{20}$-aryl)$_2$ group, a B($C_1$–$C_{10}$-alkyl)$_2$ group, a B($C_6$–$C_{20}$-aryl)$_2$ group, a $C_1$–$C_{10}$-alkyl group, a $C_1$–$C_{10}$-fluoroalkyl group, a $C_6$–$C_{20}$-aryl group, a $C_6$–$C_{20}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{14}$ and $R^{15}$ together with the atoms connecting them form a ring system, $M^2$ is silicon, germanium or tin and z is 0 or 1, $R^x$ and $R^y$ are identical or different and are each a four-membered group having the formula

[Formula with R^5–R^9]

where $R^5$, $R^6$, $R^7$, $R^8$ and $R^9$ are identical or different and are each a hydrogen atom, a halogen atom or a $C_1$–$C_{40}$-group such as an Si($C_1$–$C_{10}$-alkyl)$_3$ group, an Si($C_6$–$C_{20}$-aryl)$_3$ group, an N($C_1$–$C_{10}$-alkyl)$_2$ group, an N($C_6$–$C_{20}$-aryl)$_2$ group, a B($C_1$–$C_{10}$-alkyl)$_2$ group, a B ($C_6$–$C_{20}$-aryl)$_2$ group, a $C_1$–$C_{10}$-alkyl group, a $C_1$–$C_{10}$-fluoroalkyl group, a $C_6$–$C_{20}$-aryl group, a $C_6$–$C_{20}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or in each case two radicals $R^5$, $R^6$, $R^7$, $R^8$ and $R^9$ together with the atoms connecting them form a ring system, l+n+p=2, and m+o=1.

2. A metallocene of the formula I as claimed in claim 1, wherein $M^1$ is zirconium or hafnium, $R^1$ and R are identical and are each a halogen atom or a $C_1$–$C_4$-alkyl group, $R^3$ are identical and are each a $C_1$–$C_4$-alkyl group, $R^4$ are identical and are each a hydrogen atom, $R^{13}$ is

[Formulas]

where $M^2$ is silicon or germanium, $R^{14}$ and $R^{15}$ are identical or different and are each a $C_1$–$C_{10}$-alkyl or $C_6$–$C_{10}$-aryl group, z is equal to 1 and $R^x$ and $R^y$ are identical.

3. A metallocene of the formula I as claimed in claim 1 which is a bis-(dihydroindenyl)zirconocene.

4. A process for preparing a metallocene of the formula I as claimed in claim 1, which comprises:

(a) preparing a compound of the formula I'

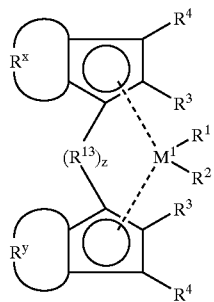

(I)

wherein ring A and ring B are fully unsaturated, so that ring A and ring B are the substituted or unsubstituted six-member rings of indenyl ligands, and wherein $R^{x1}$ and $R^{y1}$ are defined in the manner of $R^x$ and $R^y$ of claim 1, except that $R^{x1}$ is a four-member, di-terminally unsaturated precursor of $R^{x1}$, and $R^{y1}$ is a four-member, di-terminally unsaturated precursor of $R^y$, and (b) partially hydrogenating ring A and ring B to obtain a compound of the formula I of claim 1 having dihydroindenyl ligands in place of ligands containing ring A and ring B.

5. A catalyst comprising a) at least one metallocene of the formula I as claimed in claim 1, and b) at least one cocatalyst.

6. A catalyst as claimed in claim 5, wherein the cocatalyst is an aluminoxane.

7. A catalyst as claimed in claim 5, wherein the metallocene is supported and/or prepolymerized.

8. A process for preparing a polyolefin which comprises polymerizing an olefin in the presence of the catalyst as claimed in claim 5.

9. A process as claimed in claim 2, wherein, in said formula I, l+n=2, m=1, and o and p=0.

10. A metallocene as claimed in claim 9, wherein l=1, m=1, and n=1.

11. A metallocene as claimed in claim 9, wherein l=2, m=1, and n=0.

12. A metallocene as claimed in claim 9, wherein l=0, m=1, and n=2.

13. A metallocene as claimed in claim 2, wherein $R^{13}$ is

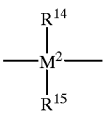

wherein $M^2$ is Si and $R^{14}$ and $R^{15}$ are identical and a $C_1$-alkyl.

14. A catalyst comprising a) at least one metallocene as claimed in claim 13, and b) at least one cocatalyst.

15. A catalyst as claimed in claim 14, wherein the cocatalyst is an aluminoxane.

16. A catalyst as claim 15, wherein the metallocene is supported and/or prepolymerized.

17. A process for preparing an olefin which comprises polymerizing an olefin in the presence of the catalyst as claimed in claim 14.

18. A process for preparing a polyolefin which comprises polymerizing an olefin in the presence of the catalyst as claimed in claim 15.

19. A process for preparing a polyolefin which comprises polymerizing an olefin in the presence of the catalyst as claimed in claim 16.

* * * * *